(12) United States Patent
Layouni et al.

(10) Patent No.: US 10,328,409 B2
(45) Date of Patent: Jun. 25, 2019

(54) METHODS FOR PERFORMING FLOW REACTIONS UTILIZING HIGH TEMPERATURE HYDROFLUORIC ACID

(71) Applicant: Corning Incorporated, Corning, NY (US)

(72) Inventors: Khaled Layouni, Painted Post, NY (US); Olivier Lobet, Villiers sous Grez (FR)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 15/560,355

(22) PCT Filed: Mar. 24, 2016

(86) PCT No.: PCT/US2016/023911
§ 371 (c)(1),
(2) Date: Sep. 21, 2017

(87) PCT Pub. No.: WO2016/154384
PCT Pub. Date: Sep. 29, 2016

(65) Prior Publication Data
US 2018/0104665 A1    Apr. 19, 2018

(30) Foreign Application Priority Data

Mar. 26, 2015 (EP) .................................. 15305448

(51) Int. Cl.
*B01J 19/00* (2006.01)
*B01J 19/02* (2006.01)
*C07C 13/00* (2006.01)

(52) U.S. Cl.
CPC ....... *B01J 19/0093* (2013.01); *B01J 19/0013* (2013.01); *B01J 19/0073* (2013.01);
(Continued)

(58) Field of Classification Search
CPC ..... B01J 19/00–19/0013; B01J 19/0053; B01J 19/0073; B01J 19/0093; B01J 2219/00049;
(Continued)

(56) References Cited

U.S. PATENT DOCUMENTS 5,690,763 A    11/1997  Ashmead et al.
2005/0214184 A1    9/2005  Chambers et al.
(Continued)

FOREIGN PATENT DOCUMENTS

DE    102006001327 A2    5/2007

OTHER PUBLICATIONS

EFUNDA: The Ultimate Online Reference for Engineers; http://www.efunda.com/; Downloaded Oct. 25, 2017; 2 Pages.
(Continued)

*Primary Examiner* — Natasha E Young
(74) *Attorney, Agent, or Firm* — Gregory V. Bean

(57) ABSTRACT

A method of performing a reaction is disclosed comprising flowing a reaction mixture (50) comprising HF past a compression seal (40) within a flow reactor (20), wherein the compression seal (40) includes an O-ring or gasket (30, 32) and where the O-ring or gasket (30, 32) comprises fluoroelastomer (to include fluoroelastomers and perfluoroelastomers), while maintaining the reaction mixture comprising HF at a temperature of 50° C. or greater [generally at a temperature in the range of from 50° C. and greater (60, 70, 80, 90, 100, 120, 150, and 180° C.) up to 220° C.], using O-rings or gaskets (30, 32) that comprise a fluoroelastomer having a pre-use tensile strength in the range of from 0.1 to 14 MPa measured according to IS037, and desirably further having a compressive set in the range of from 0 to 12% measured according to IS0815.

17 Claims, 1 Drawing Sheet

(52) U.S. Cl.
CPC ............. *B01J 19/02* (2013.01); *C07C 13/00* (2013.01); *B01J 2219/00051* (2013.01); *B01J 2219/0086* (2013.01); *B01J 2219/00761* (2013.01); *B01J 2219/00783* (2013.01); *B01J 2219/00813* (2013.01); *B01J 2219/00824* (2013.01); *B01J 2219/00833* (2013.01); *B01J 2219/00867* (2013.01)

(58) Field of Classification Search
CPC .... B01J 2219/00051; B01J 2219/00761; B01J 2219/00801; B01J 2219/0081; B01J 2219/00813; B01J 2219/00819; B01J 2219/00824; C07C 13/00
See application file for complete search history.

(56) References Cited

U.S. PATENT DOCUMENTS

| | | |
|---|---|---|
| 2012/0040448 A1 | 2/2012 | Gremetz et al. |
| 2012/0114534 A1 | 5/2012 | Van Der Heijden |

OTHER PUBLICATIONS

Eriks; Technical Handbook; http://o-ring.info/en/downloads/technical-handbook; Downloaded Oct. 25, 2017; 2 Pages.

International Search Report and Written Opinion of the International Searching Authority; PCT/US2016/023911; dated May 31, 2016; 12 Pages; European Patent Office.

James Walker 'O' Ring Guide, Issue 7; http://www.jameswalker.biz/es/pdf_docs/3-o-ring-guide; Downloaded Oct. 25, 2017; 32 Pages.

Parker O-Ring Handbook; http://www.parker.com/literature/ORD% 205700%20Parker_O-Ring_Handbook.pdf; Downloaded Oct. 25, 2017; 289 Pages.

Precision Polymer Engineering; Elastomer Sealing Solutions Experts; http://www.prepol.com/; Downloaded Oct. 25, 2017; 9 Pages.

Dupont Performance Elastomers; "Perfluoroelastomer and Fluoroelastomer Seals for Photovoltaic Cell Manufacturing Processes"; Paper Presented at the Intersolar SMET, May 2009; 12 Pages.

Kimura et al; "Development of Photocatalytic Reactor Having Light Source Inside by Electrical Discharge"; 21st International Symposium on Plasma Chemistry (ISPC 21) Aug. 2013; 4 Pages.

METHODS FOR PERFORMING FLOW REACTIONS UTILIZING HIGH TEMPERATURE HYDROFLUORIC ACID

This application claims the benefit of priority under 35 U.S.C. § 371 of International Patent Application Serial No. PCT/US16/23911, now WO2016/154384, filed on Mar. 24, 2016, which in turn, claims the benefit of priority under 35 U.S.C. § 119 of European Patent Application Serial No. 15305448.1, filed on Mar. 26, 2015, the contents of each or which are relied upon and incorporated herein by reference in their entireties.

FIELD

The field of this disclosure is methods for performing flow reactions involving the use of hydrofluoric acid ("HF"), particularly for performing reactions using high temperature (such as 50° C., 120° C., 150° C., 180° C. and higher) HF-containing mixtures and reactors employing non-permanent fluidic interconnections in the form of compression seals.

BACKGROUND

Flow reactors, specifically small channel flow reactors comprising passage sizes of sub-millimeter up to about 1 or 2 centimeters hydraulic diameter offer advantages over conventional batch reactors, including significant improvements in energy efficiency, reaction control, safety, reliability, productivity, scalability and portability. In such small-dimension flow reactors, the chemical reactions typically take place continuously, in confinement within micro- or milli-scale channels. Small reaction volumes and large surface area to volume ratios and the small in-process reaction mixture volumes provide orders of magnitude improvements in mass and heat transfer relative to batch reactors, as well improved safety and decreased environmental impact. Such reactors lend themselves well to process intensification, including well-controlled operation of reaction chemistries or reaction conditions unachievable in batch.

A flow reactor generally comprises assembly of several individual or stacked fluidic modules. Fluidic connections between the fluidic modules, if non-permanent, are generally comprised of conduits in the form of piping and O-ring or gasket based compressive seals. O-rings or gaskets may also be employed between modules stacked directly together or between layers within individual disassemblable modules.

In order to assure reactor reliability during use, all reactor materials have to be sufficiently compatible with the chemistry of the reaction to be performed. In particular, the conduit and reactor components and any O-rings and/or gaskets need to withstand any corrosive media used in desired reactions. Piping may be made of either stainless steel or titanium or fluoropolymers (PTFE, PFA for e.g.), for instance.

SUMMARY

While reactions benefitting from a high temperature hydrofluoric acid (HF) environment may be somewhat rare, the use of small channel flow reactors opens the way to safe and controlled operation of new reactions and of old reactions under new conditions. Although O-ring manufacturers provide general guidance regarding chemical resistivity and temperature performance, such guidance is typically rather general, and is not particular to high temperature HF environments. The present inventors have found that the performance of O-rings or gaskets having similar compositions and ratings for chemical resistance can vary widely when subjected to high temperature HF-containing mixtures. It is desirable, however, to be able to reliably conduct high temperature (50° C. and above) HF-containing reactions in reactors having elastomer seals in the reactor modules and/or piping. Accordingly, it is useful to establish the material properties and process conditions needed to reliably perform such reactions or processes in reactors employing elastomer seals.

According to one aspect of the present disclosure, a method of performing a reaction having a reaction mixture comprising HF (hydrofluoric acid) in a flow reactor at a temperature of 50° C. or greater, is provided. The method includes flowing a reaction mixture comprising HF past a compression seal within a flow reactor, where the flow reactor includes first and second reactor components formed of one or more HF-resistant materials, and where the compression seal includes an O-ring or gasket positioned between the first and second reactor components, and where the O-ring or gasket comprises fluoroelastomer (defined as including fluoroelastomers and perfluoroelastomers for purposes of this disclosures). The method further includes maintaining the reaction mixture comprising HF at said temperature of 50° C. or greater, advantageously at a temperature in the range of from 50 to 220° C., and is performed with O-rings or gaskets that comprise a fluoroelastomer having a pre-use tensile strength in the range of from 0.1 to 14 MPa measured according to ISO37.

According to further aspect of the present disclosure, the O-rings or gaskets comprise a fluoroelastomer that also has a pre-use compressive set in the range of from 0 to 12% measured according to ISO815.

Other further embodiments, features, and advantages of the present disclosure will be described below.

DETAILED DESCRIPTION

Figure 1:
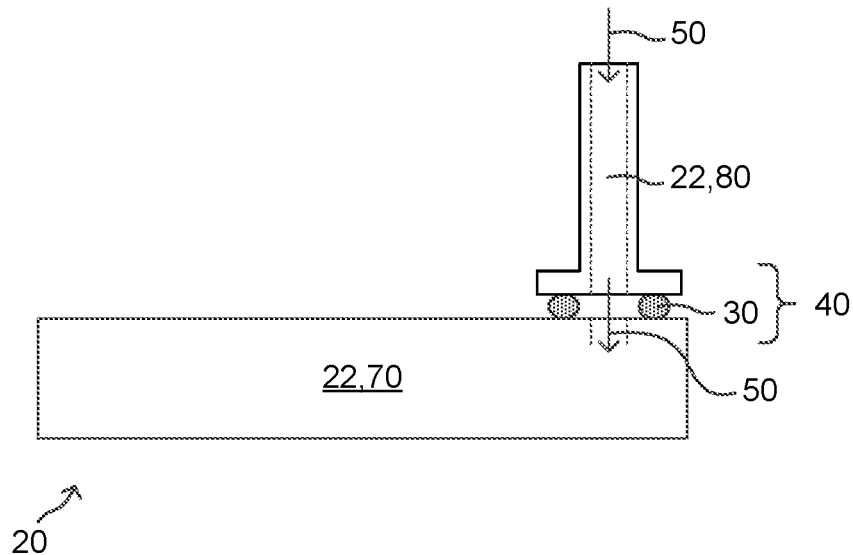
FIG. 1 is a schematic diagram of a portion of a modular flow reactor in which the methods of the present disclosure may be practiced.

Reference will now be made in detail to the accompanying drawings which illustrate certain instances of the devices and methods described generally herein. Whenever possible, the same reference numerals will be used throughout the drawings to refer to the same or like parts.

FIG. 1 is schematic diagram of a portion of a modular flow reactor 20, including first and second reactor components 22 in this case in the form of a reactor module 70 and a fluid conduit 80. The module 70 and the conduit 80 are pressed together (by structures such as screw fittings, springs, or the like, not shown in the figure) against O-ring 30, positioned between them, forming thereby a compression seal 40. The O-ring 30 surrounds respective openings or ports, such as indicated by the dashed lines in the figure, in the module 70 and the fitting 80, providing a fluidic connection between module 70 and fitting 80.

Figure 2:
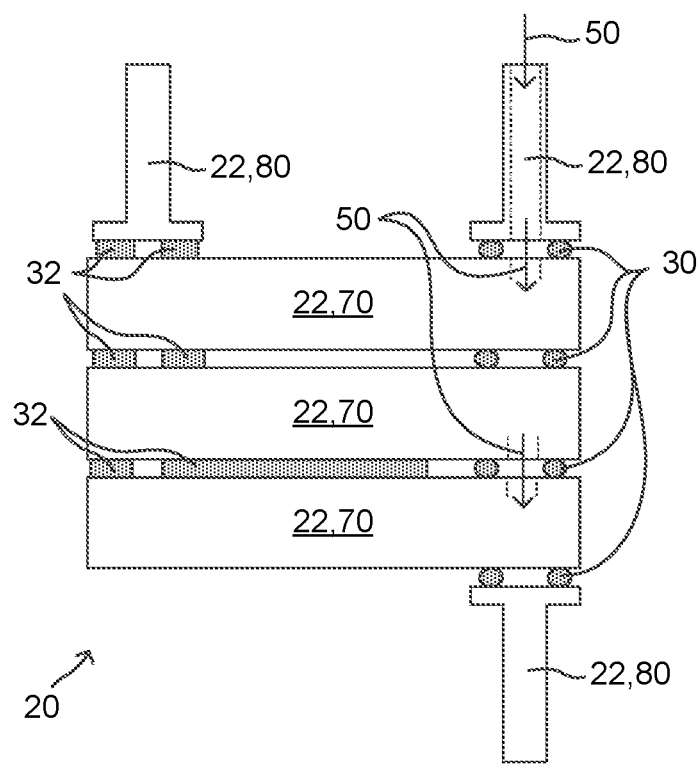
FIG. 2 is a schematic diagram of a modular flow reactor including the structures of FIG. 1.

FIG. 2 is a schematic diagram of a modular flow reactor 20 including the structures of FIG. 1 and some additional reactor components in the form of both modules 70 and conduits 80.

According to the work of the present inventors, durability of fluoroelastomers used for O-rings or gaskets in high temperature HF solutions is associated with the pre-use physical properties of the material—specifically with pre-use tensile strength and compressive set. According to one embodiment of the inventive disclosure, to provide reasonable durability for use in HF at temperatures from 50° C. up to 220° C., the fluoroelastomer material employed should have tensile strength in the range of from 0.1 to 14 MPa (measured according to according to ISO37). According to a further embodiment, in addition to the tensile strength in the range of from 0.1 to 14 MPa, the compressive set of the fluoroelastomer (measured according to ISO815) should be in the range of from 0 to 12%. By using fluoroelastomer materials with these physical properties, reaction can be performed using reaction mixtures containing HF at temperatures in the range of from 50° C. and greater (e.g., from 60, 70, 80, 90, 100, 120, 150, and 180° C.) up to 220° C.; reaction can be performed at temperatures in the range of from 50° C. up to 220° C. or less (e.g. up to 150° C., 180° C.); reaction can more particularly be performed in the ranges of from 120° C. to 180° C., of from 150° C. to 180° C. or from 120° C. to 150° C.

In particular, and with reference to FIGS. 1 and 2, the inventors have established and demonstrated a method of performing a reaction having a reaction mixture comprising HF (hydrofluoric acid) in a flow reactor at a temperature of 50° C. or greater in which the method comprises: (1) flowing a reaction mixture (50) comprising HF past a compression seal (40) within a flow reactor (20), the flow reactor comprising first and second reactor components (22) formed of one or more HF-resistant materials, the compression seal (40) comprising an O-ring or gasket (30, 32) positioned between the first and second reactor components (22), the O-ring or gasket (30, 32) comprising a fluoroelastomer; and (2) maintaining the reaction mixture (50) comprising HF at said temperature of 50° C. or greater, advantageously at a temperature in the range of from 50 to 220° C. Further according to the method, the O-rings or gaskets (30, 32) comprise a fluoroelastomer having a pre-use tensile strength in the range of from 0.1 to 14 MPa measured according to ISO37.

As a further extension of the method, the O-rings or gaskets (30, 32) comprise a fluoroelastomer further having a pre-use compressive set in the range of from 0 to 12% measured according to ISO815.

Where particularly high chemical resistance is desired, ceramics including non-transparent ceramics and in particular silicon carbide, for its high chemical durability and high thermal conductivity, is desirable.

EXPERIMENTAL

Various chemically O-rings rated as highly chemically resistant and rated for use with HF were obtained. Details of composition are generally not shared by the manufacturers, but physical data including tensile strength and compressive set are generally provided, or can be readily measured. Table 1 below shows the results of exposure to HF (40 wt. % HF in water) at the indicated temperatures for 160 continuous hours. An "O" represents a surviving O-ring, while an X represents an O-ring sufficiently damaged to be unusable, or destroyed. The asterisk represents an intermediate level of nonetheless significant damage.

As may be seen from the results shown in Table 1, only those fluoroelastomers having both low tensile strength and low compressive set have high durability in HF. In particular, the ability of fluoroelastomers having both low tensile strength and low compressive set to withstand HF for 160 hours at even 220° C. indicates that fluoroelastomers with these properties will be expected to have proportionally even longer lifetimes (and longer relative to other fluoroelastomers) at lower temperatures.

TABLE 1

| Trade Name | Tensile Strength (MPa) | Compressive Set (%) | Degrees C. for 160 hours continuous exposure | | | | |
|---|---|---|---|---|---|---|---|
| | | | 50 | 120 | 150 | 180 | 220 |
| Chemraz 505 | 12 | 25 | O | O | O | * | X |
| Chemraz 585 SD | 42.6 | 35 | X | | | | |
| Sephat FPM80 | 12.9 | 11.5 | O | O | O | O | O |
| Kalrez 7075 | 17.91 | 12 | O | O | O | X | |
| Perlast G75TX | 14 | 8 | O | O | O | O | O |
| Perlast G75S | 19 | 20 | X | | | | |

The methods and/or devices disclosed herein are generally useful in performing any process that involves mixing, separation, extraction, crystallization, precipitation, or otherwise processing fluids or mixtures of fluids, including multiphase mixtures of fluids—and including fluids or mixtures of fluids including multiphase mixtures of fluids that also contain solids—within a microstructure. The processing may include a physical process, a chemical reaction defined as a process that results in the interconversion of organic, inorganic, or both organic and inorganic species, a biochemical process, or any other form of processing.

It will be apparent to those skilled in the art that various modifications and variations can be made without departing from the spirit or scope of the invention.

The invention claimed is:

1. A method of performing a reaction having a reaction mixture comprising HF (hydrofluoric acid) in a flow reactor at a temperature of 50° C. or greater, the method comprising:
   flowing a reaction mixture (50) comprising HF past a compression seal (40) within a flow reactor (20), the flow reactor comprising first and second reactor components (22) formed of one or more HF-resistant materials, the compression seal (40) comprising an O-ring or gasket (30, 32) positioned between the first and second reactor components (22), the O-ring or gasket (30, 32) comprising a fluoroelastomer; and
   maintaining the reaction mixture (50) comprising HF at said temperature of at least 50° C., wherein the O-rings or gaskets (30, 32) comprise a fluoroelastomer having a pre-use tensile strength in the range of from 0.1 to 14 MPa measured according to ISO37.

2. The method according to claim 1 wherein the O-rings or gaskets (30, 32) comprise a fluoroelastomer having a pre-use compressive set in the range of from 0 to 12% measured according to ISO815.

3. The method according to claim 1, wherein the step of maintaining the reaction mixture (50) comprising HF at a temperature of at least 50° C. comprises maintaining the reaction mixture (50) at a temperature in the range of from 60° C. to 220° C.

4. The method according to claim 1, wherein the step of maintaining the reaction mixture (50) comprising HF at a temperature of at least 50° C. comprises maintaining the reaction mixture (50) at a temperature in the range of from 70° C. to 220° C.

5. The method according to claim 4, wherein the step of maintaining the reaction mixture (50) comprising HF at a temperature of at least 50° C. comprises maintaining the reaction mixture (50) at a temperature in the range of from 120° C. to 180° C.

6. The method according to claim 4, wherein the step of maintaining the reaction mixture (50) comprising HF at a temperature of at least 50° C. comprises maintaining the reaction mixture (50) at a temperature in the range of from 150° C. to 180° C.

7. The method according to claim 1, wherein the step of maintaining the reaction mixture (50) comprising HF at a temperature of at least 50° C. comprises maintaining the reaction mixture (50) at a temperature in the range of from 80° C. to 220° C.

8. The method according to claim 1, wherein the step of maintaining the reaction mixture (50) comprising HF at a temperature of at least 50° C. comprises maintaining the reaction mixture (50) at a temperature in the range of from 90° C. to 220° C.

9. The method according to claim 1, wherein the step of maintaining the reaction mixture (50) comprising HF at a temperature of at least 50° C. comprises maintaining the reaction mixture (50) at a temperature in the range of from 100° C. to 220° C.

10. The method according to claim 1, wherein the step of maintaining the reaction mixture (50) comprising HF at a temperature of at least 50° C. comprises maintaining the reaction mixture (50) at a temperature in the range of from 120° C. to 220° C.

11. The method according to claim 1, wherein the step of maintaining the reaction mixture (50) comprising HF at a temperature of at least 50° C. comprises maintaining the reaction mixture (50) at a temperature in the range of from 150° C. to 220° C.

12. The method according to claim 1, wherein the step of maintaining the reaction mixture (50) comprising HF at a temperature of at least 50° C. comprises maintaining the reaction mixture (50) at a temperature in the range of from 180° C. to 220° C.

13. The method according to claim 1, wherein the step of maintaining the reaction mixture (50) comprising HF at a temperature of at least 50° C. comprises maintaining the reaction mixture (50) at a temperature in the range of from 50° C. to 150° C.

14. The method according to claim 1 wherein the step of maintaining the reaction mixture (50) comprising HF at a temperature of at least 50° C. comprises maintaining the reaction mixture (50) at a temperature in the range of from 50° C. to 180° C.

15. The method according to claim 1, wherein the step of maintaining the reaction mixture (50) comprising HF at a temperature of at least 50° C. comprises maintaining the reaction mixture (50) at a temperature in the range of from 120° C. to 150° C.

16. The method according to claim 1, wherein the HF-resistant materials comprise ceramic.

17. The method according to claim 16 wherein the HF-resistant materials comprise silicon carbide.

* * * * *

UNITED STATES PATENT AND TRADEMARK OFFICE
CERTIFICATE OF CORRECTION

PATENT NO. : 10,328,409 B2
APPLICATION NO. : 15/560355
DATED : June 25, 2019
INVENTOR(S) : Khaled Layouni et al.

Page 1 of 1

It is certified that error appears in the above-identified patent and that said Letters Patent is hereby corrected as shown below:

In the Specification

In Column 1, Line 10 (approx.), delete "or" and insert -- of --, therefor.

Signed and Sealed this
Seventeenth Day of December, 2019

Andrei Iancu
*Director of the United States Patent and Trademark Office*